US008153359B2

(12) United States Patent
Strehl et al.

(10) Patent No.: US 8,153,359 B2
(45) Date of Patent: Apr. 10, 2012

(54) TOXICITY ASSAY BASED ON HUMAN BLASTOCYST-DERIVED STEM CELLS AND PROGENITOR CELLS

(75) Inventors: Raimund Strehl, Gothenburg (SE); Sarah Adler, Berlin (DE)

(73) Assignee: Cellartis AB, Gothenburg (SE)

( * ) Notice: Subject to any disclaimer, the term of this patent is extended or adjusted under 35 U.S.C. 154(b) by 78 days.

(21) Appl. No.: 12/444,017

(22) PCT Filed: Oct. 2, 2007

(86) PCT No.: PCT/EP2007/008576
§ 371 (c)(1),
(2), (4) Date: Oct. 28, 2009

(87) PCT Pub. No.: WO2008/040532
PCT Pub. Date: Apr. 10, 2008

(65) Prior Publication Data
US 2010/0047842 A1    Feb. 25, 2010

Related U.S. Application Data

(60) Provisional application No. 60/849,583, filed on Oct. 2, 2006, provisional application No. 60/903,775, filed on Feb. 26, 2007.

(51) Int. Cl.
*C12Q 1/00* (2006.01)
*G01N 33/53* (2006.01)
*C12N 5/00* (2006.01)
*C12N 5/02* (2006.01)
*C12N 5/08* (2006.01)

(52) U.S. Cl. .............. 435/4; 435/7.1; 435/325; 435/371

(58) Field of Classification Search .............. 435/4, 7.1, 435/325, 371
See application file for complete search history.

(56) References Cited

U.S. PATENT DOCUMENTS

| | | | |
|---|---|---|---|
| 5,616,122 A | 4/1997 | Lam et al. |
| 2002/0012905 A1* | 1/2002 | Snodgrass |
| 2003/0073654 A1 | 4/2003 | Goffe et al. |
| 2004/0259254 A1* | 12/2004 | Honmou et al. |
| 2005/0031599 A1 | 2/2005 | Kooy et al. |
| 2005/0064586 A1* | 3/2005 | Sheng et al. |
| 2006/0073587 A1 | 4/2006 | Stice et al. |

FOREIGN PATENT DOCUMENTS

| | | |
|---|---|---|
| WO | WO 03/055992 A2 | 7/2003 |
| WO | WO 2006/044204 A2 | 4/2006 |
| WO | WO 2006/070370 A2 | 7/2006 |
| WO | WO 2007/120699 A2 | 10/2007 |

OTHER PUBLICATIONS

Spielmann et al., 2001, Toxicology in Vitro, vol. 15, p. 585-590.*
International Preliminary Report on Patentability (PCT/IB/373) dated Apr. 7, 2009.

Adler, S., et al., Human Embryonic Stem Cells for in vitro Developmental Toxicity Testing, XP002464533.
34th Annual Conference of the European Teratology Society, 3rd-6th Sep. 2006, Abano Terme, Padova, Italy, Reproductive Toxicology, 2006, vol. 22, No. 2, pp. 263-288.
Laschinski, G., et al., Cytotoxicity Test Using Blastocyst-Derived Euploid Embryonal Stem Cells: A New Approach to In Vitro Teratogenesis Screening, Reproductive Toxicology, 1991, vol. 5, pp. 57-64.
Adler, S., et al., The Detection of Differentiation-inducing Chemicals by Using Green Fluorescent Protein Expression in Genetically Engineered Teratocarcinoma Cells, Alternatives to laboratory animals (ATLA) 2005; 33(2): 91-103.
Cho, Y.M., et al., Dynamic changes in mitochondrial biogenesis and antioxidant enzymes during the spontaneous differentiation of human embryonic stem cells, Biochemical and Biophysical Research Communications, 2009: 348(4): 1472-1478.
De Sesso, J.M., et al., Observations on the histopathogenesis of 5-fluorouracil developmental toxicity in New Zealand white rabbits and its amelioration by TTI, a functional analog of one carbon metabolism. Teratology 1995: 51, p. 172.
Evans, S.M., et al., Development of a high throughput in vitro toxicity screen predictive of high acute in vivo toxic potential, Toxicology in Vitro 2001; 15(4-5):579-84.
Genschow, E., et al., Validation of the embryonic stem cell test in the International ECVAM validation study on three in vitro embryotoxicity tests. ATLA, 2004; 32(3): 209-44.
Gilbert, S.F., Developmental Biology, Sinauer Associates, Inc., Sunderland, Massachusetts, 2003: 750 pp. (1 page included herewith).
Heins, N., et al., Derivation, Characterization, and Differentiation of Human Embryonic Stem Cells, Stem Cells 2004; 22:367-376.
Laschinski, G., et al., Cytotoxicity test using blastocyst-derived euploid embryonal stem cells: a new approach to in vitro teratogenesis screening, Reproductive Toxicology, (Elmsford, NY) 1991; 5(1):57-64. Ross, S.A., et al., Retinoids in embryonal development, Physiological Reviews, 2000, 80(3): 1021-54.
Soprano, D.R., et al., Retinoids as Teratogens, Annual Review of Nutrition, 1995: 15:111-32.
Stacey, G.N., et al., The development of 'feeder' cells for the preparation of clinical grade hES cell lines: Challenges and solutions, Journal of Biotechnology, 2006; 125(4): 583-8.
Stephens, J.D., et al., Multiple congenital anomalies in a fetus exposed to 5-fluorouracil during the first American Journal of Obstetrics and Gynecology, 1980; 15; 137(6): 747-9.
Anon. Regulation (EC) No. 1907/2006 of the European Parliament and of the council; European Communities; http://eur-lex.europa.eu/LexUriServ/site/en/oj/2006/I_396/I_39620061230en00010849.pdf (p. 1 of 849).
International Search Report (PCT/ISA/210) dated Jan. 15, 2008.
S. Bakand et al., "Toxicity Assessment of Industrial Chemicals and Airborne Contaminants: Transition from in Vivo to in Vitro Test Methods: A Review," 17 Inhalation Toxicology 775-787 (2005).
A. Castano et al., "Correlations Between the RTG-2 Cytotoxicity Test EC50 and in Vivo LC50 Rainbow Trout Bioassay," 32(11) Chemosphere 2141-2157 (1996).
T. Riss et al., "Use of Multiple Assay Endpoints to Investigate the Effects of Incubation Time, Dose of Toxin, and Plating Density in Cell-Based Cytotoxicity Assays," 2(1) Assay and Drug Development Technologies 51-62 (2004).

* cited by examiner

*Primary Examiner* — Shin-Lin Chen
(74) *Attorney, Agent, or Firm* — Buchanan Ingersoll & Rooney PC

(57) ABSTRACT

An in vitro toxicity assay based on human blastocyst-derived stem cells for the detection of toxicity in the human species is provided, which enables novel detection of in vitro human toxicity for a substance and/or more efficiently detects human toxicity compared to non-human assays. Furthermore, the detection of toxicity for substances is enabled, which is known to display inter-species differences and the toxic effect was not detectable by toxicological tests in mice.

13 Claims, 5 Drawing Sheets

TOXICITY ASSAY BASED ON HUMAN BLASTOCYST-DERIVED STEM CELLS AND PROGENITOR CELLS

BACKGROUND OF THE INVENTION

Figure 1:
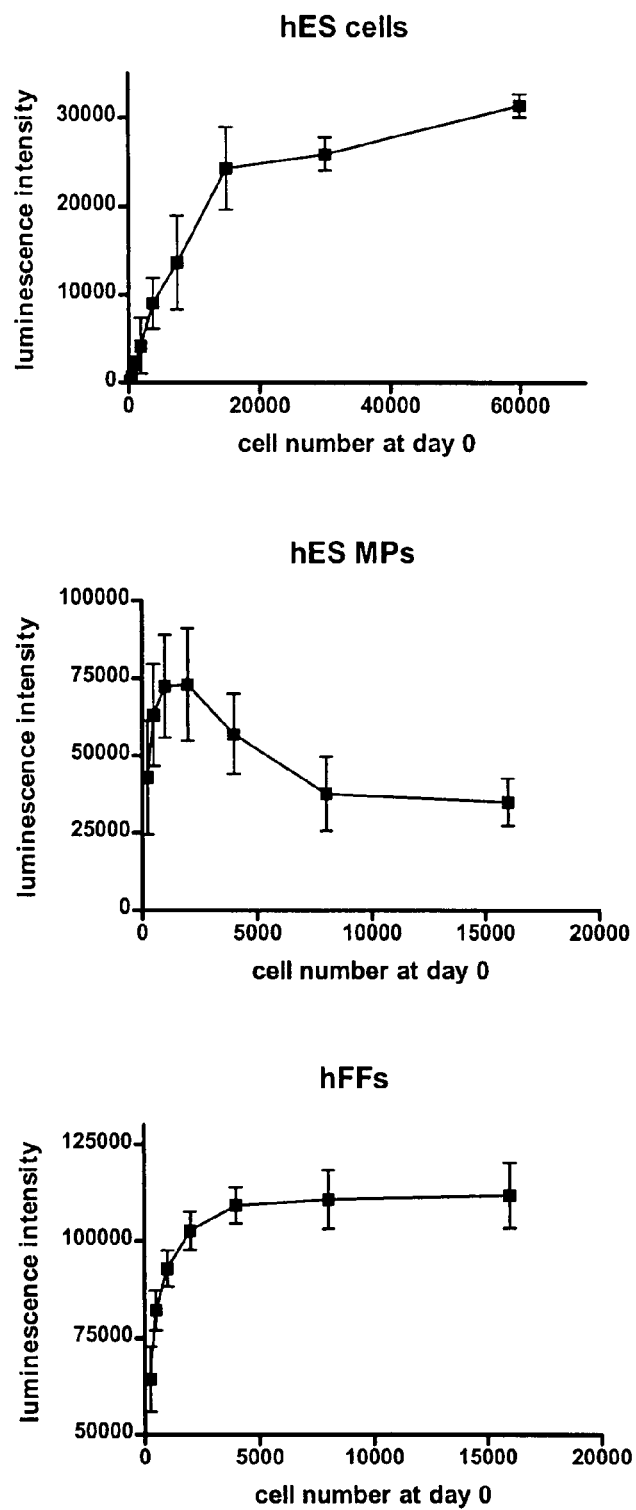

Human blastocyst-derived stem (hBS) cells have the unique ability to differentiate into derivatives of all three germ layers. This characteristic turns them into an exceptional tool in the field of toxicology as they can serve as a "cell factory" for functional cells (Moon S Y, et al, *Mol Ther* 13(1):514, 2006). Moreover, effects of compounds interacting during the process of hBS cell differentiation can be detected which makes them especially valuable in the field of developmental toxicology.

As the new European Chemicals Policy (REACH) will come into effect in 2007, toxicological information is required for more than 30.000 chemicals manufactured or imported in volumes above 1 ton annually (Anon, 2007). Consequently, around 3.9 million additional test animals will potentially be used and the costs to industry are estimated to be around 1.5 Billion Euro, of which 32% are attributed alone to developmental toxicity studies (RPA, 2002). Therefore, in vitro developmental toxicity tests are urgently needed. In addition, the pharmaceutical industry faces the demand for high throughput in vitro toxicity tests as reliable toxicological data for novel drug candidates have to be generated as early as possible in the development phase. The reduction of the high attrition rates due to incorporation of early in vitro toxicity screenings would reduce the associated costs enormously. Moreover, a number of substances are known to display significant inter-species differences and lead to severe malformations in humans but not distinctly in mice or rats, e.g. 13-cis retinoic acid (Isotretinoin) that is used in the treatment of severe acne (Accutane, Roche) and the sedative and anti-inflammatory drug thalidomide (Contergan) (Gilbert, 2003). Thus, human relevant developmental toxicity tests are required.

One of the most promising in vitro embryotoxicity tests to date is the validated embryonic stem cell test (EST), which employs murine embryonic stem (mES) cells to assess the embryotoxic potential of chemicals. The EST takes the different sensitivities of mES cells and murine fibroblasts to embryotoxicants into account. In addition, the differentiation of mES cells into functional cardiomyocytes serves as a toxicological endpoint (Genschow, 2004). However, the EST still aims to predict human toxicity in an animal system.

The use of human embryonic stem cells in a developmental toxicity test could provide reliable, human relevant data that add value to existing toxicity tests for safety assessment of drugs and chemicals. However, the application of hBS cells in toxicity testing is challenging as these cells require complex handling techniques. For example, hBS cells need to be seeded in cell aggregates instead of single cells to ensure their growth and show variable attachment capacities to surfaces that results in high variances. Additionally, the population-doubling time of hBS cells is with 36 hours significantly longer than that of mES cells with 12 hours. Another important difference between mouse and human BS cells are their culturing requirements. To maintain mES cells in an undifferentiated state the addition of leukaemia inhibitory factor (LIF) to the culture medium is sufficient. hBSC lines, however, are cultured on a mouse or human feeder layer, which appears to be the most reliable way to maintain cells stably in the undifferentiated state. Much work is being done to find feeder-free culture systems but these are at an early stage of development (Stacey et al, 2006)

The present invention represents a toxicity assay based on hBS cells for prediction of human toxicity, such as developmental toxicity and cytotoxicity. The present invention shows a great advantage over mES cells being able to deliver human relevant data that help identifying human teratogens of which some are known to display inter-species differences as for example 13-cis retinoic acid. Such a toxicity test would have the potential to be part of a testing strategy for the detection of human relevant developmental toxicants.

DESCRIPTION OF THE INVENTION

Definitions and Abbreviations

"Assay" or "assays" are intended to describe in vitro tests performed to measure cytotoxicity and/or developmental toxicity on e.g. genetic, protein or functional level.

As used herein, the term "blastocyst-derived stem cell" is denoted BS cell, and the human form is termed "hBS cells" ors "hBSC".

As used herein the terms "progenitor" or "progenitor cell type" are any cell derived form hBS cells at any stage of differentiation between the undifferentiated hBS cell and a fully differentiated cell.

By the terms "feeder cells" or "feeders" are intended to mean cells of one type that are co-cultured with cells of another type, to provide an environment in which the cells of the second type can grow. The feeder cells may optionally be from a different species as the cells they are supporting. The feeder cells may typically be inactivated when being co-cultured with other cells by irradiation or treatment with an anti-mitotic agent such as mitomycin c, to prevent them from outgrowing the cells they are supporting. Without limiting the foregoing, one specific such feeder cell type may be a human feeder, such as a human skin fibroblast, here denoted as hFF. In the context of the present invention hFF also exemplifies an adult cell type. Another feeder cell type may be mouse embryonic fibroblasts (mEF).

The interpretation of the term "substance" is not intended to be limited to therapeutic agents (or potential therapeutic agents), or agents with documented toxicity effects such as neurotoxins, hepatic toxins, toxins of hematopoietic cells, myotoxins, carcinogens, teratogens, or toxins to one or more reproductive organs. The term substances may further be chemical compositions such as agricultural chemicals, e.g. pesticides, fungicides, fertilizers, or as well be components used in cosmetics.

The term "IC50" value stands in the present context for the concentration of a test substance that leads to 50% death of tested cells in vitro.

"Efficiency" or "efficient", if not otherwise defined, are in the context of an assay herein intended to mean that—the said assay is more likely to detect substances being toxic in human, and/or that the toxic concentrations, such as the corresponding IC50 values analyzed, are closer to known human in vivo data, whenever available, in comparison to methods or assays described in the prior art, such as assays based on mouse embryonic stem cells or mouse carcinoma cells.

SHORT DESCRIPTION OF THE INVENTION

The present invention relates to an in vitro toxicity assay based on human blastocyst-derived stem cells for the detection and/or prediction of toxicity in the human species, wherein the assay enables novel detection of toxicity of a substance and/or more efficiently detects toxicity compared to non-human assays or assays based on adult human cell types.

The present invention also relates to an in vitro toxicity assay based on human progenitor cells derived from blastocyst-derived stem cells for the detection and/or prediction of toxicity in the human species, wherein the assay enables novel detection of toxicity for a substance and/or more efficiently detects toxicity compared to non-human assays or assays based on adult human cell types.

One further aspect of the present invention is an in vitro toxicity assay comprising at least two human cell types, such as at least three, at least four, at least five human cell types selected from a group comprising of human blastocyst-derived stem cells, human progenitor cells and human adult-like cells for the detection and/or prediction of toxicity in the human species, wherein the assay enables novel detection of toxicity for a substance and/or more efficiently detects toxicity compared to non-human assays or assays based on adult human cell types. Specifically the assay of the present invention can predict differential toxicity: e.g. a higher degree of toxicity to embryonic cells than to adult cells Still one further aspect of the present invention is an in vitro toxicity assay based on human blastocyst-derived stem cells for the detection of toxicity in the human species, which more efficiently predicts human toxicity, such as embryotoxicity, of 13-cis retinoic acid (13CRA) compared to non-human assays.

Still one further aspect of the present invention is an in vitro toxicity assay based on human progenitor cells derived from blastocyst-derived stem cells, such as human blastocyst stem cell-derived mesenchymal progenitors (hBS-MPs), for the detection of toxicity in the human species, which more efficiently predicts human toxicity of all trans retinoic acid (ATRA) compared to adult human cells, such as hFF.

The present invention also relates to a method/an assay to detect and/or predict in vitro toxicity in the human species for a substance by exposing one or more populations of human blastocyst-derived stem cells to said substance, the method comprising the steps of
(i) seeding of cells in multi well format plates
(ii) exposing of seeded cells to one or more concentrations of one/or more substances
(iii) analyzing of cytotoxic and/or embryo toxic endpoints.
(iv) optional, correlating to known in vivo toxicity data.

The present invention also relates an additional method to detect and/or predict in vitro toxicity in the human species for a substance by exposing one or more populations of human progenitor cells to said substance, the method comprising the steps of
(i) seeding of cells in multi well format plates
(ii) exposing of seeded cells to one or more concentrations of one/or more substances
(iii) analyzing of cytotoxic and/or embryo toxic endpoints
(iv) optional, correlating to known in vivo toxicity data.

The present invention also relates to a method/an assay to detect and/or predict in vitro toxicity in the human species for a substance by exposing one or more populations of human blastocyst-derived stem cells to said substance, the method comprising the steps of
(i) human blastocyst-derived stem cells seeded into one or more wells of one or more multi well plates
(ii) a mature human cell type seeded into separate wells of the multi well plate(s) in (i) or into one or more wells of one or more separate plates
(iii) optionally one or more progenitor population derived from human blastocyst-derived stem cells each seeded into separate wells of the multi well plates in (i) and/or (ii) or into one or more wells of one or more separate multi well plates,
provided that the seeding density allows the cells to substantially maintain its proliferating capacity until the time point for conducting the measurements of one or more effects of one or more substances, which have been exposed to the cells.

The present invention also relates to a method/an assay to detect and/or predict in vitro toxicity in the human species for a substance by exposing one or more populations of human blastocyst-derived stem cells to said substance, the method comprising the steps of
(i) one or more progenitor population derived from human blastocyst-derived stem cells each seeded into one or more multi well plates
(ii) an mature human cell type seeded into separate wells of the multi well plate(s) in (i) or seeded into one or more separate plates
provided that the seeding density allows the cells to substantially maintain its proliferating capacity until the time point for conducting the measurements of one or more effects of one or more substances, which have been exposed to the cells.

The present invention also relates to a method/an assay to detect and/or predict in vitro toxicity in the human species for a substance by exposing one or more populations of human blastocyst-derived stem cells to said substance, the method comprising the steps of
(i) human blastocyst-derived stem cells seeded into one or more wells of one or more multi well plates
(il) one or more progenitor populations derived from human blastocyst-derived stem cells each seeded into one or more multi well plates in (i) or seeded into one or more separate plates provided that the seeding density allows the cells to substantially maintain its proliferating capacity until the time point for conducting the measurements of one or more effects of one or more substances, which have been exposed to the cells.

DETAILED DESCRIPTION OF THE INVENTION

Human blastocyst stem cells provide a unique tool for developmental toxicity testing and therefore, we have according to the present invention developed a hBS cell based developmental toxicity test, such as a developmental toxicity assay and a cytotoxicity assay. As a proof of concept, a toxicity assay with the endpoint viability was developed employing pluripotent hBS cells, hBS cell derived mesenchymal progenitors (hBS MPs) and human foreskin fibroblasts (hFFs) that represent three different degrees of developmental maturation. A set of developmental toxicants with well-known in vivo data, i.e. all-trans retinoic acid (ATRA) and 13-cis retinoic acid (13CRA), was tested employing two different viability assays, i.e. ATP content and resazurin (RES) reduction. Besides, 5-Fluorouracil (5-FU) was used as a positive and Saccharin as a negative control.

Retinoids like ATRA and 13CRA are mainly used in the treatment of cancer and dermatological diseases as acne or psoriasis. Characteristic patterns of retinoid induced malformations comprise defects of craniofacial structures including the central nervous system, the limbs, the thymus and the axial skeleton (Ross et al, 2000). While ATRA and 13CRA are both severe teratogens in humans, their teratogenic potential in murine systems differs (Nau et al, 2001). 13CRA shows a much lower teratogenic potential in mice in vivo and lower differentiation inducing capacities in murine teratocarcinoma (P19) cells in vitro than ATRA (Adler et al, 2005; Soprano and Soprano 1995). Therefore, these structurally related substances were chosen to challenge our test system. The anticancer drug 5-FU is a developmental toxicant both in vivo and in vitro (Jacob et al, 1986) and individual reports exist on 5-FU related birth defects in humans (Stephens et al, 1980).

One embodiment of the invention relates to a cytotoxicity test based on hBS cells, hBS cell derived progenitor cells and/or human foreskin fibroblasts, representing cells from different differentiation levels or a combination thereof. This test based on cytotoxicity as an endpoint is efficient in the detection of some human developmental toxicants including all-trans retinoic acid (ATRA) and 13-cis retinoic acid (13CRA). These substances displayed low IC50 values in undifferentiated blastocyst-derived stem cells and progenitor cells, compared to higher values in adult human cells.

The present invention also relates to an in vitro toxicity assay based on human blastocyst-derived stem cells for the detection and/or prediction of toxicity in the human species. The assay enables novel detection of toxicity, specifically toxicity to embryonic or developing cells, for a substance and/or more efficiently detects and/or predicts toxicity in human, compared to non-human assays or assays based on adult human cell types.

The invention further relates to an in vitro toxicity assay based on human progenitor cells derived from blastocyst-derived stem cells for the detection and/or prediction of toxicity in the human species, wherein the assay enables novel detection of toxicity for a substance and/or more efficiently detects and/or predicts toxicity in human, compared to non-human assays or assays based on adult human cell types. The progenitor cells according to the present invention may be any progenitor cell between a hBS cell and a fully differentiated cell. Suitable progenitor cells in the present invention may be mesodermal, endodermal, or ectodermal cell types. The progenitor cells may further be mesenchymal progenitor cells, fibroblast-like progenitor cells, cardiac progenitor cells, hepatic progenitor cells, pancreatic progenitor cells or neural progenitor cells.

In a specific embodiment of the present invention the progenitor cells are human blastocyst stem cell derived mesenchymal progenitors (hBS-MPs).

Figure 3:
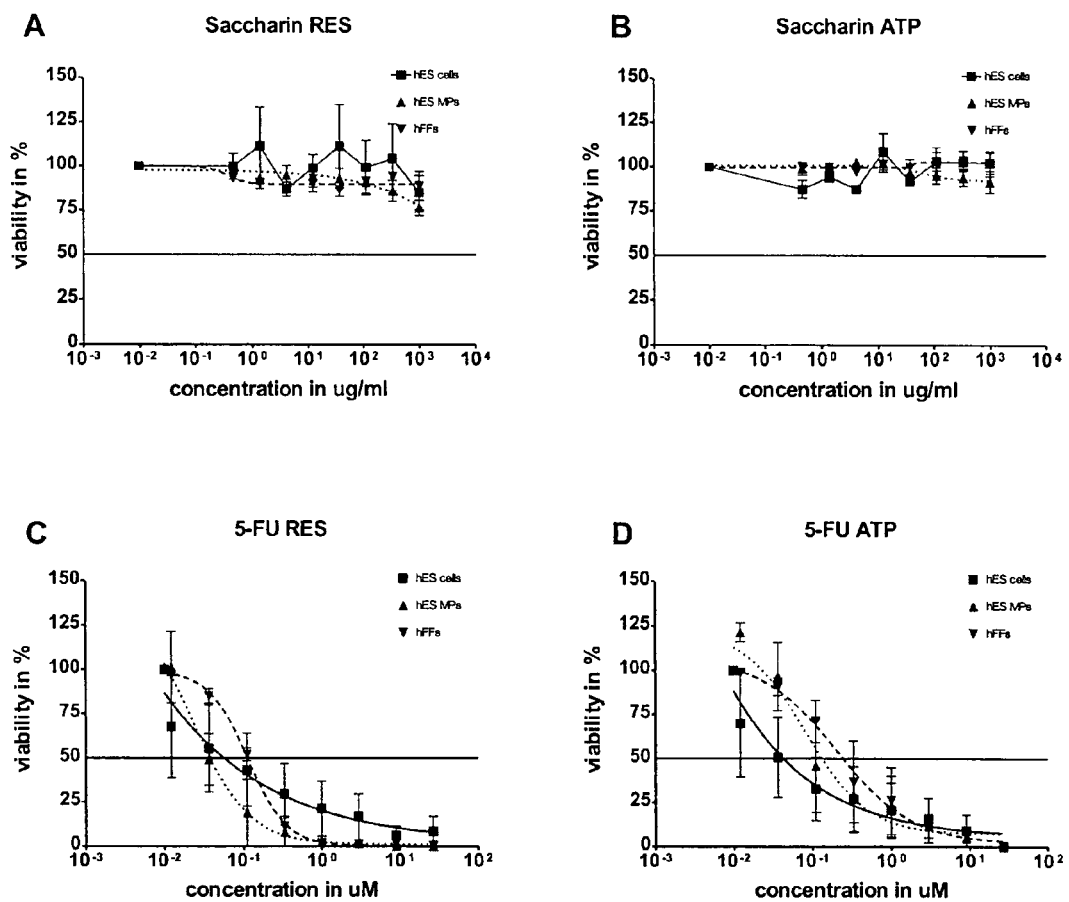
Figure 4:
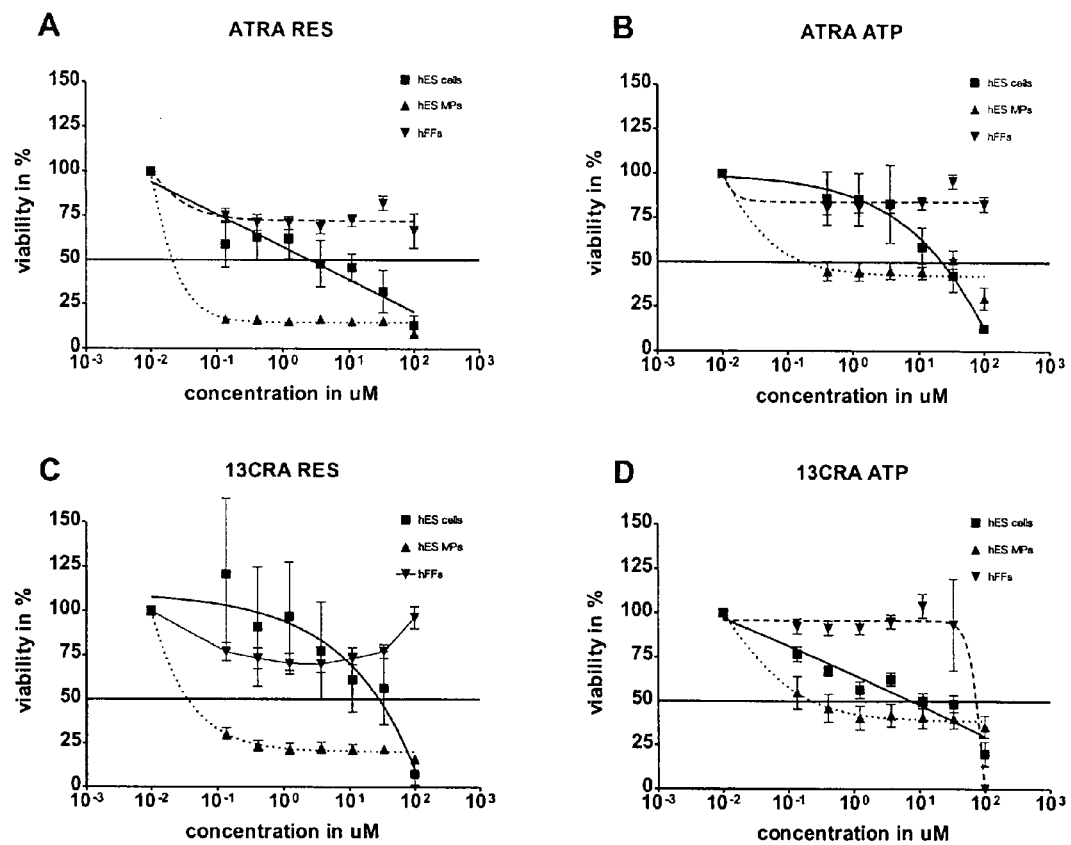

Comparisons of IC50 values shows that the hBS cells and hBS derived progenitor cells are more sensitive towards toxic substances, such as 5-FU, ATRA and 13CRA than adult mature cell types, such as hFF cells (see FIGS. 3 and 4). The progenitor cells represent an easily cultured hBS derived cell type enabling larger scale culture by enzymatic passaging, while still maintaining a higher sensitivity to toxic substances.

The present invention further relates to an assay comprising at least two human cell types, such as at least three, at least four, at least five, human cell types. These human cell types may be selected from a group comprising hBS cells, progenitor cells and adult-like cells. The adult-like cells may be derived from different human tissue, such as skin and muscle. The adult-like cells may also be derived from different stages of development, such as neonatal or adult. In a specific embodiment of the present invention the adult-like cells used are human foreskin fibroblasts from a newly born baby boy.

The present invention further relates to an in vitro toxicity assay wherein the assays of non-human species may be of any non-human mammalian origin, such as mouse, rat, or pig. Mouse assays in turn may be exemplified by mouse embryonic stem cell-based assays or mouse teratocarcinoma cell-based assays.

The non-human assay, referred to as a reference system to this application, may also be an in vivo assay. Such an in vivo assay may be an animal model of e.g. mouse, rat, rabbit, pig or dog.

More specifically the present invention relates to an in vitro toxicity assay based on human blastocyst-derived stem cells for the detection and/or prediction of toxicity in the human species, wherein the assay enables novel detection of toxicity for a substance and/or more efficiently, such as at least 50%, at least 75% more or, at least 2 times, at least 5 times, at least 10 times, at least 30 times, at least 50 times, at lest 75 times, at least 100 times more efficiently detects toxicity compared to non-human assays.

In a specific embodiment of the present invention, the in vitro toxicity assay detects toxicity 123 times more efficiently compared to a non-human assay based on mouse teratocarcinoma cells.

Equivalently, the present invention relates to an in vitro toxicity assay based on human blastocyst-derived stem cells for the detection and/or prediction of toxicity in the human species, wherein the assay enables novel detection of toxicity for a substance and/or more efficiently, such as at least 1.5, at least 4, at least 10 times more efficiently detects toxicity, specific toxicity to embryonic cells, when comparing hBS cells and progenitor cells, and at least 2, such as at least 4, at least 10 times more efficiently detects toxicity when comparing hBS cells and adult-like fibroblast cells, and at least 1.5, at least 2, at least 5, at least 10 times more efficiently detects toxicity when comparing progenitor cells and adult-like fibroblast cells.

Furthermore, the assay of the present invention may be based on cytotoxic endpoints, such as measurement of viability. Suitable detecting techniques for such endpoints may be chosen from a group measuring metabolic activity including ATP content analysis, MTT salt analysis and Resazurin conversion.

Additional suitable endpoints of the present invention can be chosen from a group of embryo toxic endpoints. The expression levels of biomolecules on either the genetic level or protein level may be analyzed, such as genomics and proteomics measurements of RNA, enzyme and antibody levels. MicroRNA levels may further be analyzed. Suitable means for measuring both cytotoxicity and embryo toxicity can be colorimetry (quantifiable change in visible color) or fluorometry (quantifiable change in fluorescence). The measurement may be performed in multi-well plate reader wherein the content of several wells are analyzed simultaneously. The test is designed to allow scale up for medium to high throughput application. One other suitable set-up for detection and quantified measurement of toxic effects may be performed in High Content Reader.

In one embodiment of the invention the powerful screening technology high-content screening (HCS) is used. HCS expands the ability of identifying and quantifying compound effects on a number of cellular events in a manner that allows for the rapid screening of substances. HCS allows multiple measurements simultaneously within a single screening platform. It enables to automate the tasks associated with microscopic studies like data capture and analysis together with the capacity to quantify specific cellular events with the throughput of multi-well sample preparation.

According to the present invention in developmental toxicity testing, HSC enables to detect influences on the differentiation into all three germ layers in parallel with cytotoxicity in one and the same test plate in a relevant biological system. Time depending effects of substances on living cells is examined as well, employing HCS providing a valuable tool to study toxicokinetics and affected pathways.

In one embodiment of the invention, when employing hBSC in toxicology testing the cells may need to be seeded in small aggregates in order to be maintained in a proliferative stage. This is generally causing interferences in the toxicity testing, as high variances in cell numbers from one well to the other may occur. Employing the technique of HCS it is possible to normalize measured signals to the number of cells per test well.

In a specific embodiment of the present invention cytoxicity is measured by Resazurin conversion.

In another embodiment of the present invention cytoxicity is measured by ATP content analysis.

Still another specific embodiment of the present invention relates to an in vitro toxicity assay based on human blastocyst-derived stem cells for the detection of toxicity in the human species, which more efficiently detects human toxicity of 13CRA compared to non-human assays.

In yet another embodiment of the present invention genetically engineered cell lines, such as undifferentiated hBS cell lines, hBS derived progenitor cell types or somatic-like hBS cell, derived types can by used. Such engineered cell lines can be reporter cell lines expressing fluorescent or other markers under the control of developmentally relevant promoters.

In addition, the present invention relates to a method to detect and/or predict in vitro toxicity in the human species for a substance by exposing one or more populations of human blastocyst-derived stem cells to said substance, the method comprising the steps of
(i) seeding of cells in multi well format plates
(ii) exposing of seeded cells to one or more concentrations of one/or more substances
(iii) analyzing of cytotoxic and/or embryo toxic endpoints.
(iv) optional, correlating to known in vivo toxicity data.

The present invention also relates to a method/an assay to detect and/or predict in vitro toxicity in the human species for a substance by exposing one or more populations of human blastocyst-derived stem cells to said substance, the method comprising the steps of
(i) human blastocyst-derived stem cells seeded into one or more wells of one or more multi well plates
(ii) a mature human cell type seeded into separate wells of the multi well plate(s) in (i) or into one or more wells of one or more separate plates
(iii) optionally one or more progenitor population derived from human blastocyst-derived stem cells each seeded into separate wells of the multi well plates in (i) and/or (ii) or into one or more wells of one or more separate multi well plates, provided that the seeding density allows the cells to substantially maintain its proliferating capacity until the time point for conducting the measurements of one or more effects of one or more substances, which have been exposed to the cells.

In addition, the present invention relates to a method to detect and/or predict in vitro toxicity in the human species for a substance by exposing one or more populations of human blastocyst-derived stem cells to said substance, the method comprising the steps of (i) one or more progenitor population derived from human blastocyst-derived stem cells each seeded into one or more multi well plates
(ii) an mature human cell type seeded into separate wells of the multi well plate(s) in (i) or seeded into one or more separate plates
provided that the seeding density allows the cells to substantially maintain its proliferating capacity until the time point for conducting the measurements of one or more effects of one or more substances, which have been exposed to the cells.

In addition, the present invention relates to a method to detect and/or predict in vitro toxicity in the human species for a substance by exposing one or more populations of human blastocyst-derived stem cells to said substance, the method comprising the steps of (i) human blastocyst-derived stem cells seeded into one or more wells of one or more multi well plates
(iI) one or more progenitor populations derived from human blastocyst-derived stem cells each seeded into one or more multi well plates in (i) or seeded into one or more separate plates provided that the seeding density allows the cells to substantially maintain its proliferating capacity until the time point for conducting the measurements of one or more effects of one or more substances, which have been exposed to the cells.

During this time differentiation of the seeded hBS derived cells may be observed to e.g. progenitor types from all germ layers such as, cardiac precursors, hepatocyte like progenitor cells and neuronal progenitors.

One other embodiment of the present invention also relates to a method to detect and/or predict in vitro toxicity in the human species for a substance by exposing one or more populations of human progenitor cells to said substance, the method comprising the steps of
(i) seeding of cells in multi well format plates
(ii) exposing of seeded cells to one or more concentrations of one/or more substances
(iii) analyzing of cytotoxic and/or embryo toxic endpoints
(iv) optional, correlating to known in vivo toxicity data.

The assay can be performed in multiwell plate format 1536, 384, 96, 48, 24, 12, 6 well. In the case of 96 well plates, the number of seeded cells in step (i) range from 1 cell to 1M cells, preferably 1,000-100,000 and more preferably 10,000-30,000 cells per well. The wells of the plates in any of the steps (i) may further be pre/post-coated with proteins, peptides or extra-cellular matrix components.

The exposure of the cells in step (ii) may be performed for a period of 1 min to 60 days, preferably 5 minutes to 30 days, 1 day to 20 days and more preferably 5-15 days.

The toxicity analysis of step (iii) may be performed by any suitable endpoint described herein.

The obtained in vitro data may in step (iv) be further be compared to in vivo data by a mathematical prediction model or algorithm therefore.

One specific embodiment of the present invention relates to a method to detect and/or predict in vitro toxicity in the human species for a substance by exposing one or more populations of human blastocyst-derived stem cells to said substance, the method comprising the steps of
(i) seeding of cells in non-coated or coated multi well format tissue culture plates
(ii) exposing of seeded cells to several concentrations of a substance for a period of 10 days
(iii) analyzing by measuring ATP content or Resazurin conversion In another aspect, the invention relates to use of an assay as herein in drug discovery and/or for safety assessment studies.

In still further aspects, the present invention relates to use of an assay as described herein for embryo toxicity, teratogenecity studies and/or for the evaluation of substances identified by the European REACH legislation.

The present invention also relates to a kit for detecting toxicity in human as described herein or for use of a method as also described herein, said kit comprising
(i) human blastocyst-derived stem cells
(ii) (optional) positive and negative control substances
(iii) a user manual.

A kit of the present invention may further comprise at least one additional human cell type selected from a group comprising of progenitor cells and adult-like fibroblasts.

The present invention also relates to a kit for detecting toxicity in human as described above or for use in a method as also described above, said kit comprising
(i) progenitor cells derived from human blastocyst-derived stem cells
(ii) (optional) positive and negative control substances
(iii) a user manual.

One embodiment of the invention is a kit including hBS, or an hBS cell derived cell type which is optionally genetically engineered or optionally in combination with germ layer specific antibodies, together with an algorithm, such as an high content screening algorithm for detecting quantitatively a panel of developmental toxicity relevant endpoints in combination with an endpoint for general cytotoxicity

FIGURE LEGENDS

FIG. 1. Proliferation curves for hBS cells (A), hBS MPs (B) and hFFs (C) determined by measuring to intracellular ATP content which is directly proportional to number of viable cells at day 10. The proliferation test was performed in four independent runs for hFFs and hBS MPs (n=4) and in two independent runs for hBS cells (n=2). The error bars describe the standard error of the mean.

Figure 2:
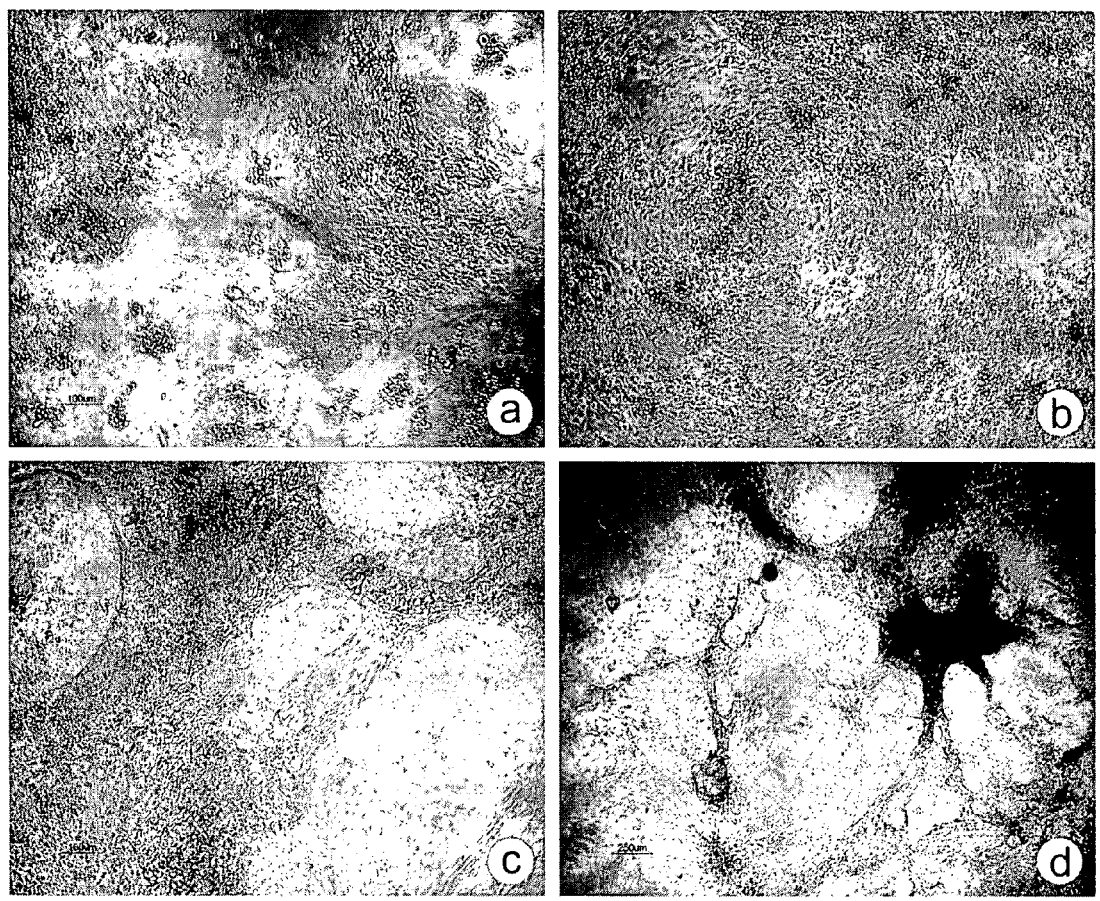

FIG. 2. Phase contrast micrographs of hBS cell growth and differentiation in 96 well plates monitored at (a) day 1, (b) day 4, (c) day 7 and (d) day 10. Seeding density 60.000 cells/well at day 0.

FIG. 3. Concentration response curves for the negative control substance Saccharin (A, B) and the positive control substance 5-FU (C, D) employing three cell types, hFFs, hBS MPs and hBS cells. The data were obtained by measuring RES reduction (A, C) and intracellular ATP content per well (B, D) and were normalized to the untreated/solvent control. All experiments were performed in three independent runs (n=3). The error bars describe the standard error of the mean. The error bars describe the standard error of the mean. All the experiment were performed in three independent runs.

FIG. 4. Concentration response curves for the substances ATRA (A, B) and 13-CRA (C, D) employing three cell types, hFFs, hBS MPs and hBS cells. The data were obtained by measuring RES reduction (A, C) and intracellular ATP content (B, D) per well and were normalised to the untreated/solvent control. All experiments were performed in at least three independent runs (nX3). The error bars describe the standard error of the mean. For ATRA and 13-CRA the hBS cells and the progenitor cells show a higher sensitivity to the toxic substance than the hFF. The IC50 ratios between hBS and progenitor cells are 10 000:1 (ATRA) and 4000:1 (13-CRA). Between hBS cells and hFF the IC50 values are more than 1:4 (ATRA) and more than 1:6 (13-CRA).

Figure 5:
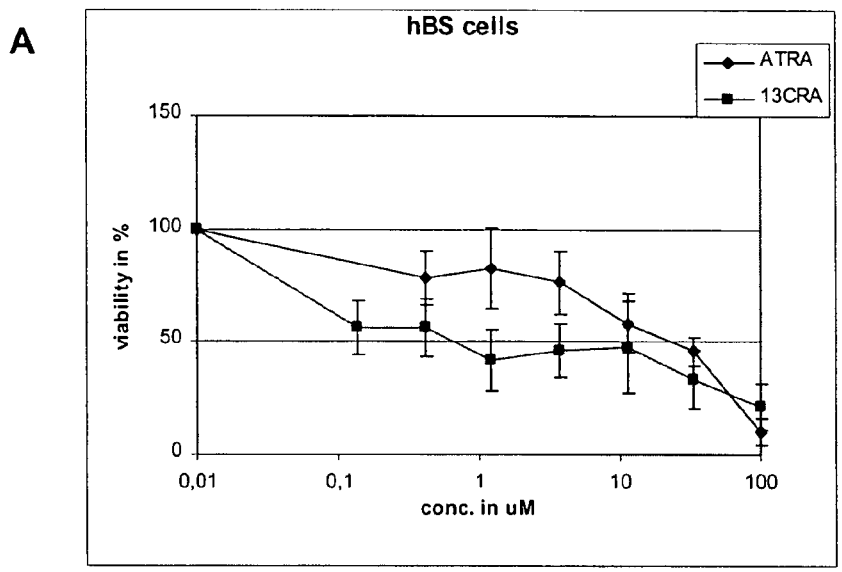
Figure 5:
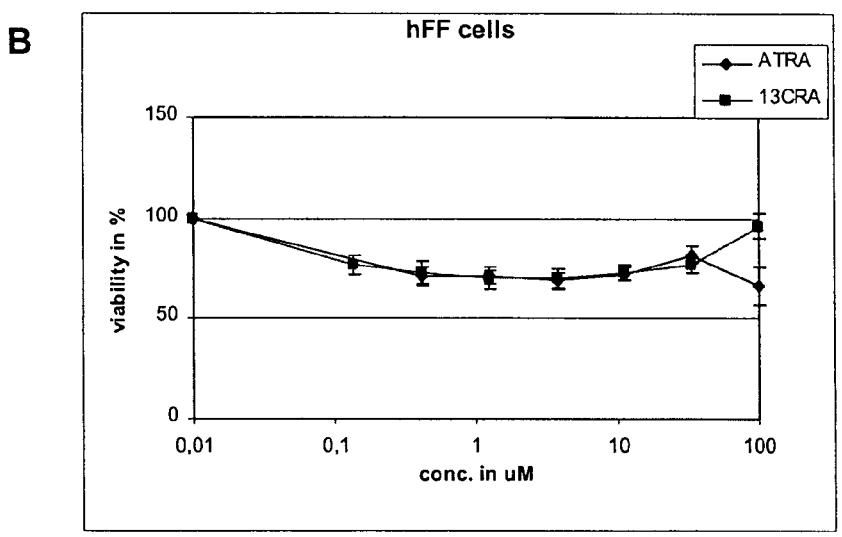

FIG. 5 a) shows the concentration response curve for ATRA and 13CRA in undifferentiated hBS cells after 10 days exposure using an ATP assay. The IC50 values for ATRA and 13CRA are 30.38 µM and 15.85 µM respectively. FIG. 5 b) shows the dose-response curve for ATRA and 13CRA (13-cis retinoic acid) in hFFs after 10 days exposure using an ATP assay. The IC50 values for ATRA and 13CRA are 244.3 µM and 301.6 µM respectively.

EXAMPLES

Example 1

Culture of hBS Cells, Progenitor Cells and hFF Cells

The hBS cell lines SA002 and SA002.5 were established and characterised as described previously (Heins et al., 2004, WO03055992), and registered at NIH (http://stemcells.nih.gov/research/registry/cellartis.asp) and UK Stem Cell Bank (http://www.mrc.ac.uk/Utilities/Documentrecord/index.htm?d=MRC003259). The cell lines were maintained on mitomycin-C inactivated mouse embryonic fibroblasts (mEF) in VitroHES™ medium (Vitrolife, Kungsbacka, Sweden) supplemented with 4 ng/ml human recombinant basic fibroblast growth factor (bFGF) (Invitrogen, Carlsbad, Calif.). Undifferentiated hBS cells were passaged every 4-5 days by mechanical dissociation using the Swemed Stem Cell Tool (Swemed Lab International AB, Bilidal, Sweden).

Fibroblast-like progenitor cells were generated by cutting out pieces of hBS cell colonies in 200×200 µm pieces and placing of the pieces in Petri dishes for aggregation in a medium based of KO-DMEM, 20% FCS, 1% Glutamax, 1% NEAA, 1% PEST and 0.1 mM β-mercaptoetanol (all from Gibco Initrogen). Floating aggregates were formed over a period of four days and thereafter plated at high density of approximately 10 aggregates per well in tissue culture dishes coated with gelatine. The outgrowths were observed and the cells further dissociated at day 5-14 and passaged at a 1:1 split at the first passage. When the cultures had reached confluence the split ratio was normally set to 1:2. The medium used for subculture after plating the aggregates were composed of DMEM high glucose without natriumpyruvat+glutamax, 10% FCS, 4 ng/ml bFBF, 1% PEST.

Human blastocyst stem cell derived mesenchymal progenitors (hBS-MPs) were obtained through derivation from hBS cell line SA002.5, by the following method which comprises the steps of:
i) plating of undifferentiated hBS cells onto a surface;
ii) incubation for between 2 and 21 days, such as for 3 to 10 days, preferably 7 days, to allow differentiation;
iii) enzymatic passaging to a new surface;
iv) repeating of step (iii) until a homogenously mesenchymal morphology is obtained;
v) culture of obtained hBS-MP cells.

The hBS-MPs were prior to toxicity testings cultured in Dulbecco's modified Eagle's medium supplemented with 10% FCS (both from Gibco Invitrogen Corporation, Paisley, Scotland) and 4 ng/ml bFGF and subcultured every 4 days in a split-ratio 1:10. Culture on tissue culture T-25 flasks using tryspin (Invitorgen) for passaging.

Specifically, expandable hBS MPs were derived from the hBS cell line SA002.5. Therefore, hBS cells were enzymatically dissociated with Tryple Select™ and plated onto 0.1% gelatine coated cell culture dishes (BD Falcon/BD Biosciences, Bedford, Mass., USA) at 1.5×105 cells per cm2 in medium consisting of DMEM supplemented with 10% fetal bovine serum (FBS) and 10 ng/ml bFGF (all from Invitrogen). After 7 days of differentiation the hBS cells were subcultured enzymatically as single cells to new gelatine coated culture dishes. This procedure was repeated every 7 days until the cell population became homogeneous in morphology. A full characterisation of this cell population was performed as part of another study showing that the hBS MPs resemble cells of the embryonic mesenchyme regarding morphology and marker expression (manuscript submitted). The hBS MPs were cultured in DMEM supplemented with 10% FBS, 50 U/ml Penicillin/Streptomycin and 4 ng/ml bFGF (all Invitrogen) in uncoated tissue culture flasks (BD Falcon™, BD Biosciences) and subcultured every 4 days at a split-ratio of 1:10.

Human foreskin fibroblasts (hFF) were obtained from the American Type Culture Collection (CRL-2429 ATCC, Manassas, Va.) and cultured in Dulbecco's modified Eagle's medium supplemented with 10% FBS with subculturing every 4 days in a split-ratio 1:5. Culture on tissue culture T-25 flasks using tryspin (Invitorgen) for passaging.

Example 2

Proliferation

In order to determine the optimal cell number to be seeded per well in a 10 day toxicity test a set of proliferation tests was performed. The optimal cell number for seeding has to be in the range where the seeded number of cells is proportional to the signal at the reading day of the test. hFFs, hBS MPs and hBS cells were seeded as triplicates in DMEM supplemented with 10% FBS and 50 U/ml Penicillin/Streptomycin (all invitrogen) into gelatine (Sigma) coated 96-well plates in a 2-fold dilution series with the highest cell density being 16.000 cells/well for hFF and hBS MPs seeded as single cell suspension and 60.000 cells/well for hBS cells seeded in aggregates of 50 to 100 cells. The plates with hBSC were centrifuged for 5 min at 400 g immediately after cell seeding in order to support the reproducible attachment of the hBS cell aggregates. Culture medium was renewed on day 4 and day 7. On day 10 the intracellular ATP content in the individual wells was measured using the CellTiterGlo kit (Promega) according to the manufacturer's instructions. The test was performed in four independent runs for hFF and hBS MPs and in two independent runs for hBS cells. Additionally, the hBS cell growth was monitored daily until day 10 using an inverted microscope (Nikon, Düsseldorf, Germany). Photographs were taken at day 1, 4, 7 and 10 using a digital camera (Nikon).

The results of the proliferation test for hBS cells (FIG. 1A) show that the amount of cells per well at day 10 is directly proportional to the seeded cell number at day 0 up to a seeding density of 15.000 hBS cells/well. At higher seeding densities the curve flattens. The results of the proliferation test for hBS MPs (FIG. 1B) suggest a direct proportionality between the cell number per well at day 10 and seeded cell number up to a seeding density of 500 hBS MPs/well. At higher seeding densities the curve flattens and even falls off from a seeding density of 4000 cells/well onwards. Also the curve for hFFs (FIG. 1C) displays a direct proportionality between the cell number at day 10 and seeded cell number up to a seeding density of 500 hFFs/well and flattens at higher seeding densities. However, the curve remains at a plateau from a seeding density of 4000 cells/well onwards. Following comparison of these results, we chose suitable seeding cell numbers from the logarithmic phase of the graphs for subsequent use in the toxicity test, i.e. 500 cells/well for hFFs, 500 cells/well for hBS MPs and 5000 cells/well for hBS cells. In addition, hBS cell growth was monitored for 10 days using a phase contrast microscope (FIG. 2). The photographs demonstrate that the seeded hBS cells grow and differentiate into various tissue like structures during the 10 day period.

Example 3

Cytotoxicity Testing hBS cell colonies were dissociated into small aggregates of ca. 50 to 100 cells and seeded into gelatine coated 96-well plates (Nunc, Kamstrupvej, Denmark) in 100MI Test medium containing Knock Out DMEM supplemented with 20% FBS, 1% penicillin-streptomycin, 1% Glutamax, 0.5 mmol/l N-mercaptoethanol and 1% non-essential amino acids (all from Invitrogen) at a density of 5000 cells/well. hBS MPs and hFF cells were dissociated into single cells and seeded into gelatine coated 96-well plates (Nunc) in 100MI test medium at a density of 500 cells/well. The plates with hBSC were centrifuged directly after seeding for 5 min at 400 g.

Progenitor cells and hFF cells were dissociated into single cells and seeded into 96-well plates in 100 µl test medium.

After 24 hours the Cytotoxicity test was started by adding 100 µl toxicity solution to the test wells that had twice the concentration as the required end concentration (day 0). Toxicity medium was changed on day 4 and 7 of the assay and on day 10 the plates were analysed measuring different detection methods for cytotoxicity, i.e. measuring ATP content using Promega's CellTiterGlo Kit (Promega, Mannheim, Germany) according to the manufacturer's instructions and the reduction of Resazurin (Sigma, Stockholm, Sweden, CAS 62758-13-8) to the fluorescent Resofurin as described before (Evans et al., 2001). Both endpoints were analysed using a multi-detection reader (Fluostar Optima, BMG Labtech, Offenburg, Germany) measuring luminescence for the Cell-Titer Glo kit and fluorescence, at the wave lengths 530 nm (excitation) and 590 nm (emission) for the Resazurin assay.

Example 4

Testing of Chemicals and Statistical Analysis

The following substances were tested: 5-FU (Invivogen, Toulouse, France, CAS 51-21-8) as a positive control, Sodium Saccharin (Sigma, CAS 128-44-9) as a negative control, ATRA (Sigma, CAS 302-79-4), 13CRA (Sigma, CAS 4759-48-2). Saccharin was diluted in PBS to a concentration of 1 g/ml and stored in aliquots at 4° C. ATRA and 13CRA were dissolved in DMSO at a concentration of 0.1M and stored in aliquots at −20° C. The 5-FU solution (Invivogen) and DMSO were directly diluted in the test medium. All chemicals were tested in a 3-fold dilution series with the highest concentrations being: 27 MM for 5-FU, 1 mg/ml for Saccharin, 100 MM for ATRA and 13CRA. For ATRA and 13CRA the dilution series was performed in DMSO and the dilutions were then added to the test medium to obtain the final test concentrations. This was done to maintain an equal DMSO concentration of 0.1% in all tested ATRA and 13CRA test runs. All experiments were performed in at least three independent runs.

The IC50 values were obtained by fitting the four-parametric hill function to the data. All cell types showed a toxic reaction to 5-FU and no toxic reaction to saccharin (see FIG. 3). Comparisons of the IC50 values showed that the hBS cells and progenitor cells are much more sensitive towards the substances 5-FU, ATRA and 13CRA than the hFF cells. The progenitor cells represents an easily cultured hBS cell type enabling larger scale culture with enzymatic passaging while maintaining a higher sensitivity to toxic substances.

And more important the IC50 values for ATRA on undifferentiated hBS cells were higher than those for 13CRA, 25.76 µM and 15.85 µM respectively in the ATP assay (see FIG. 4) and 17.31 µM and 14.51 µM respectively in the Resazurin assay. The same result was found for progenitor cells where the IC50 values were dramatically decreased in comparison to hFF and hBS cells with 0.0027 µM for ATRA and 0.0004 µM for 13CRA and 0.0009 µM and 0.00002 µM respectively in the Resazurin assay.

The corresponding IC50 values previously reported in a mouse system based on pluripotent teratocarcinoma P19 cells (Adler et. al. 2005, *The detection of differentiation-inducing chemicals by using green fluorescent protein expression in genetically engineered teratocarcinoma cells, Altern Lab Anim.* 2005 April; 33(2):91-103; Adler thesis (http://w3.ub.uni-konstanz.de/v13/volltexte/2005/1619//pdf/Adler-.pdf) were 0.005 µM and 0.38 µM respectively, i.e. the mouse system fails to detect the 13CRA with a factor 123, [(IC50mouse (13CRA)/(IC50 mouse (ATRA)) is equal to 76, i.e. 0.38/0.005, while (IC50human (13CRA)/(IC50 human (ATRA)) is equal to 0.62, i.e. 15.85/25.76). Comparing the human and mouse ratios, respectively, 0.62:76 equals a factor 123.]

TABLE 1

Mean IC50 values for the tested chemicals obtained employing viability as an endpoint for human embryonic stem (hBS) cells, hBS MP and human foreskin fibroblasts (hFFs). Parameters measured were ATP content and reduction of resazurin to resofurin. All experiments were performed in at least three independent runs (n ≧ 3).

| Test Chemical | CAS No. | mean IC50 ATP | | | mean IC50 Resazurin | | |
|---|---|---|---|---|---|---|---|
| | | hFFs | hBS MPs | hBS cells | hFFs | hBS MPs | hBS cells |
| Saccharin | 82385-42-0 | No IC50 at 1 mg/ml | No IC50 at 1 mg/ml | No IC50 at 1 mg/ml | No IC50 at 1 mg/ml | No IC50 at 1 mg/ml | No IC50 at 1 mg/ml |
| 5-Fluorouracil | 51-21-8 | 0.304 µM | 0.080 µM | 0.044 µM | 0.1138 µM | 0.0423 µM | 0.045 µM |
| All-trans Retinoic Acid | 302-79-4 | No IC50 at 100 µM | 0.0027 µM | 25.76 µM | No IC50 at 100 µM | 0.0009 µM | 17.31 µM |
| 13-cis Retinoic Acid | 4759-48-2 | No IC50 at 100 µM | 0.0004 µM | 15.85 µM | No IC50 at 100 µM | 0.00002 µM | 14.51 µM |

Comparisons of the IC50 values of the two tested cell types (hBS cells and hFF) showed that the hBS cells are much more sensitive towards the substances 5-FU, ATRA and 13CRA than the hFF cells (for ATRA and 13CRA, see FIG. 4-5). The pluripotent hBS cells were by far more sensitive to ATRA and 13CRA than hFFs. These findings are consistent with previous results demonstrating a higher sensitivity of murine pluripotent cells to known teratogens than fibroblast cultures measuring viability (Laschinski et al, 1991). In addition, the IC50 values of 13-CRA were constantly lower than those of ATRA for all tested cell types in our test system. In previous in vitro teratogenicity test assays based on pluripotent murine cells, 13-CRA showed an evidently lower cytotoxic and teratogenic potential than ATRA (Adler et al, 2005). Although 13CRA is not classified as a teratogen in murine systems it is a strong teratogen in humans. Thus, our results indicate the advantage of a human cell based test system to detect human developmental toxicants over assays based on animal cells.

See also FIG. 4 for comparison between in ATP measurement of ATRA and 13CRA for the two of the cell types hBS cells and hFF. Table 2 and 3 shows the ratios between the IC50 values measured using ATP assay and the rezasurin assay respectively.

TABLE 2

Ratio between the IC50 values measured using the ATP assay

| | hBS cells | Progenitors | hFF |
|---|---|---|---|
| 5-FU | 1 | 2 | 7 |
| ATRA | 1 | 0.0001 | >4 |
| 13CRA | 1 | 0.000025 | >6 |

TABLE 3

Ratio between the IC50 values measured using the Rezasurin assay

| | hBS cells | Progenitors | hFF |
|---|---|---|---|
| 5-FU | 1 | 1 | 2.5 |
| ATRA | 1 | 0.0005 | >6 |
| 13CRA | 1 | 0.000001 | >7 |

A statistical comparison of the two different detection methods for the endpoint viability, the ATP assay and the resazurin assay, is shown in table 4.

TABLE 4

Statistical comparison of two different detection methods for the endpoint viability. Parameters measured were intracellular ATP content and resazurin reduction per well following treatment with chemicals in human foreskin fibroblasts (hFFs), hBS MPs and human embryonic stem (hBS) cells. Differences between concentration response curves were compared statistically using a two-way ANOVA test (* $p < 0.001$;  $p < 0.01$; * $p < 0.05$). Experiments were performed in at least three independent runs (n23).

| | hffs | | HBS MPs | | hBS Cells | |
|---|---|---|---|---|---|---|
| test chemical | significance | p-value | significance | p-value | significance | p-value |
| Saccharin | *** | 0.0005 | ** | 0.0043 | — | 0.6892 |
| 5-Fluorouracil | * | 0.0121 | ** | 0.0084 | — | 0.7570 |
| All-trans Retinoic Acid | *** | 0.0002 | *** | <0.0001 | — | 0.2459 |
| 13-cis Retinoic Acid | *** | <0.0001 | *** | <0.0001 | — | 0.0554 |

The similarity of the results obtained with both detection methods in hBS cells may be due to their lower proliferation rate compared to hFFs and hBS MPs. Moreover, in comparison to other cell types undifferentiated hBS cells contain fewer mitochondria while the number of mitochondria increases during their differentiation (Cho et al, 2006). Thus, the lower proliferation rate as well as the lower number of mitochondria provide an explanation for the non significant differences between the ATP and RES assay in hBS cells, which are amplified in the highly proliferative and more mitochondria containing hFFs and hBS MPs. However, both detection techniques delivered IC50 values in the same concentration range and are thus both suitable for measuring viability.

Example 4

Screening of a Set of Substances to Determine the Embryotoxicity

A selected number of test compounds are tested using the hBS cells or progenitor cells or a combination thereof in a multi-well format system. As reference system, a set of substances with different embryonic potential is selected and analysed e.g. six to ten substances. This set comprises chemicals ranging from non embryotoxic, moderate embryotoxic to strong embryotoxic. Furthermore, one negative (e.g. Saccharin) and one positive control compound (e.g. 5-Fluorouracil) is chosen.

The reference and the test substances are analysed using a testing protocol including antibodies directed against proteins involved in early differentiation and differentiation into mesoderm, endoderm and ectoderm or the expression of fluorescent proteins driven by germ layer specific promoters in genetically engineered hBSC. The right time point for analysis is crucial and therefore the time dependent expression of chosen developmental toxic endpoints is established. To quantify fluorescent signals in the test plates a High Content Reader is employed.

For the cytotoxicity endpoint IC50 values is assessed that describe the concentration of the compound that results in 50% death of cells. From the developmental toxicity endpoints, ID50 values are calculated that give the concentration of a substance that leads to 50% down-regulation of the chosen marker. These values are be compared and evaluated. In vitro embryotoxicty of the chemicals is assessed by evaluating the differences between IC50 and ID50 values for each substance. For embryotoxic substances the IC50 values are evidently higher than the ID50 values. Using these results a ranking of the reference substances and test substance enables comparison to known in vivo data.

REFERENCES

Adler S, Paparella M, Pellizzer C et al. The detection of differentiation-inducing chemicals by using green fluorescent protein expression in genetically engineered teratocarcinoma cells. Alternatives to laboratory animals: ATLA, 2005; 33(2):91-103.
Anon. Regulation (EC) No 1907/2006 of the European parliament and of the council. European Communities. Available at http://eurlex.europa.eu/LexUriServ/site/en/oj/2006/l_396/l_39620061230en00010849.pdf. Assessed Aug. 7, 2007
Cho Y M, Kwon S, Pak Y K et al. Dynamic changes in mitochondrial biogenesis and antioxidant enzymes during the spontaneous differentiation of human embryonic stem cells. Biochemical and biophysical research communications, 2006; 348(4): 1472-8.
De Sesso J M, Scialli A R, Goeringer G L. Observations on the histopathogenesis of 5-fluorouracil developmental toxicity in New Zealand white rabbits and its amelioration by TTI, a functional analog of one carbon metabolism. Teratology, 1995; 51, 172.
Evans S M, Casartelli A, Herreros E et al. Development of a high throughput in vitro toxicity screen predictive of high acute in vivo toxic potential. Toxicology in vitro. 2001; 15(4-5):579-84.
Genschow E, Spielmann H, Scholz G et al. Validation of the embryonic stem cell test in the international ECVAM validation study on three in vitro embryotoxicity tests. Alternatives to laboratory animals: ATLA, 2004; 32(3):209-44.
Gilbert S F. Developmental Biology. Sinauer Associates, Inc., Sunderland, Mass., 2003: 750 pp.
Genschow E, Spielmann H, Scholz G et al. Validation of the embryonic stem cell test in the international ECVAM validation study on three in vitro embryotoxicity tests. Alternatives to laboratory animals: ATLA, 2004; 32(3):209-44.
Heins N, Englund M C, Sjöblom C, Dahl U, Tonning A, Bergh C, Lindahl A, Hanson C, Semb 35H. "Derivation, characterization, and differentiation of human embryonic stem cells". Stem Cells 2004; 22:367-376
Laschinski G, Vogel R, Spielmann H. Cytotoxicity test using blastocyst-derived euploid embryonal stem cells: a new approach to in vitro teratogenesis screening. Reproductive toxicology (Elmsford, N.Y.), 1991; 5(1):57-64.
Ross S A, McCaffery P J, Drager U C et al. Retinoids in embryonal development. Physiological reviews, 2000, 80(3):1021-54.
RPA und Statistics Sweden. Assessment of the Business Impact of New Regulations in the Chemicals Sector. Final Report. Prepared for European Commission Enterprise Directorate General. London: RPA. 2002; -216 S.
Soprano D R and Soprano K J. Retinoids as teratogens. Annual review of nutrition, 1995; 15:111-32.
Stacey G N, Cobo F, Nieto A et al. The development of 'feeder' cells for the preparation of clinical grade hES cell lines: challenges and solutions. Journal of biotechnology, 2006; 125(4):583-8. Epub
Stephens J D, Golbus M S, Miller T R et al. Multiple congenital anomalies in a fetus exposed to 5-fluorouracil during the first trimester. American journal of obstetrics and gynecology, 1980; 15; 137(6):747-9.
WO03055992, A method for the establishment of a pluripotent human blastocyst-derived stem cell line, Cellartis A B

The invention claimed is:
1. An in vitro toxicity assay for the detection of developmental toxicity of one or more substance(s) in the human species, comprising:
    exposing said one or more substance(s) to
        (i) human blastocyst-derived stem cells ("hBS cells"),
        (ii) human foreskin fibroblasts ("hFFs"), and
        (iii) optionally, human blastocyst stem cell-derived mesenchymal progenitors ("hBS-MPs");
    measuring the toxicity of said one or more substance(s) which have been exposed to the cells; and
    comparing the data obtained for the hBS cells with those obtained for the hFFs,
    wherein said developmental toxicity is a higher degree of toxicity to hBS cells or hBS-MPs cells than to hFFs cells.
2. The in vitro toxicity assay according to claim 1, further comprising:

(i) human blastocyst-derived stem cells seeded into one or more wells of one or more multi-well plates;

(ii) human foreskin fibroblasts seeded into separate wells of said multi-well plate(s) in (i) or into one or more wells of one or more separate plates; and (iii) optionally, human blastocyst stem cell-derived mesenchymal progenitors seeded into separate wells of said multi-well plates in (i) or (ii) or both or into one or more wells of one or more separate multi-well plates, provided that the seeding density allows the cells to substantially maintain its proliferating capacity until the time point for conducting the measurements of one or more effects of one or more substance(s), which have been exposed to the cells.

3. The in vitro toxicity assay according to claim 1 or claim 2, wherein said cells are in the range of 1 cell to 1 million cells per well in a 1539-, 384-, 96-, 48-, 24-, 12-, or 6-well format.

4. The in vitro toxicity assay according to claim 3, wherein said cells are in the range of 1,000 cells to 100,000 cells per well in a 1539-, 384-, 96-, 48-, 24-, 12-, or 6-well format.

5. The in vitro toxicity assay according to claim 3, wherein said cells are in the range of 10,000 cells to 30,000 cells per well in a 1539-, 384-, 96-, 48-, 24-, 12-, or 6-well format.

6. The in vitro toxicity assay according to claim 3, wherein said cells are in the range of 10,000 cells to 20,000 cells per well in a 1539-, 384-, 96-, 48-, 24-, 12-, or 6-well format.

7. The in vitro toxicity assay according to claim 1 or claim 2, wherein said cells are incubated with said substance for a period of 1 minute to 60 days.

8. The in vitro toxicity assay according to claim 7, wherein said cells are incubated with said substance for a period of 1 minute to 30 days.

9. The in vitro toxicity assay according to claim 7, wherein said cells are incubated with said substance for a period of 5 days to 15 days.

10. The in vitro toxicity assay according to claim 7, wherein said cells are incubated with said substance for a period of 10 days.

11. The in vitro toxicity assay according to claim 1 or claim 2, wherein said toxicity is cytotoxicity or embryo toxicity.

12. The in vitro toxicity assay according to claim 1 or claim 2, wherein said toxicity is measured by colorimetry or fluorometry.

13. The in vitro toxicity assay according to claim 1 or claim 2, wherein the toxicity is visualized by Resazurin conversion, ATP content analysis, or both.

* * * * *